US012697376B2

(12) United States Patent
Huang et al.

(10) Patent No.: US 12,697,376 B2
(45) Date of Patent: Aug. 4, 2026

(54) CATIONIC LIPID COMPOUNDS

(71) Applicant: Guangzhou Anobri Pharmaceutical Co. Ltd., Guangdong (CN)

(72) Inventors: Cai Gu Huang, Guangdong (CN); Tie Qiang Huang, Guangdong (CN); Jun Rong Tan, Guangdong (CN)

(73) Assignee: Guangzhou Anobri Pharmaceutical Co. Ltd, Guangdong (CN)

( * ) Notice: Subject to any disclaimer, the term of this patent is extended or adjusted under 35 U.S.C. 154(b) by 223 days.

(21) Appl. No.: 18/681,557

(22) PCT Filed: Mar. 31, 2022

(86) PCT No.: PCT/CN2022/084270
§ 371 (c)(1),
(2) Date: Feb. 6, 2024

(87) PCT Pub. No.: WO2023/024512
PCT Pub. Date: Mar. 2, 2023

(65) Prior Publication Data

US 2024/0351974 A1 Oct. 24, 2024

(30) Foreign Application Priority Data

Aug. 23, 2021 (CN) ......................... 202110969879.0

(51) Int. Cl.

| | |
|---|---|
| ***A61K 39/00*** | (2006.01) |
| ***A61K 9/1272*** | (2025.01) |
| ***A61K 31/7105*** | (2006.01) |
| ***C07C 219/06*** | (2006.01) |

(52) U.S. Cl.
CPC ............ *A61K 39/00* (2013.01); *A61K 9/1272* (2013.01); *A61K 31/7105* (2013.01); *C07C 219/06* (2013.01)

(58) Field of Classification Search
None
See application file for complete search history.

(56) References Cited

U.S. PATENT DOCUMENTS

| | | | |
|---|---|---|---|
| 2019/0274968 A1 | 9/2019 | Weissman et al. | |
| 2019/0314524 A1 * | 10/2019 | Ansell ................... | C07C 219/06 |
| 2021/0087135 A1 | 3/2021 | Benenato et al. | |

FOREIGN PATENT DOCUMENTS

| | | | |
|---|---|---|---|
| CA | 3155015 | A1 | 3/2021 |
| CN | 108368028 | A | 8/2018 |
| WO | 2018081480 | A1 | 5/2018 |
| WO | 2018191719 | A1 | 10/2018 |
| WO | 2021030701 | A1 | 2/2021 |
| WO | 2021156267 | A1 | 8/2021 |

OTHER PUBLICATIONS

International Search Report re: WO2022084270/PCT/CN2022 Mailed Jun. 1, 2022.
Search Report for CN 202110969879.0, issued Jan. 2, 2025.

* cited by examiner

*Primary Examiner* — Celeste A Roney
(74) *Attorney, Agent, or Firm* — Parker Poe Adams & Bernstein, LLP; Elizabeth M. Crompton; Paul E. Dietze

(57) ABSTRACT

The invention relates to lipid compounds that can be used alone or in combination with other lipid components, such as neutral lipids, charged lipids, steroids, and polymer conjugated lipids to form lipid nanoparticles for delivery of therapeutic and/or prophylactic agents; pharmaceutical compositions containing the lipid nanoparticles; and methods of using the lipid nanoparticles to treat or prevent diseases.

19 Claims, No Drawings

CATIONIC LIPID COMPOUNDS

CROSS-REFERENCE TO RELATED APPLICATIONS

This application is the national stage filling under 35 U.S.C § 371 of international application number PCT/CN2022/084270, filed Mar. 31, 2022, which claims priority to Chinese patent application No. 202110969879.0, filed Aug. 23, 2021. The contents of these applications are incorporated herein by reference in their entirety.

BACKGROUND OF THE INVENTION

Effective targeted delivery of bioactive substances, such as small molecule drugs, proteins, and nucleic acids, is a persistent medical challenge. Specifically, delivery of nucleic acids to cells is difficult due to the relative instability and low cell permeability of nucleic acids. Therefore, there is a need to develop methods and compositions that facilitate delivery of therapeutic and/or prophylactic agents, such as nucleic acids to cells.

It has been demonstrated that bioactive substances, such as small molecule drugs, proteins and nucleic acids, can be efficiently transported into cells and/or intracellular compartments using lipid-containing nanoparticle compositions, liposomes, and liposome complexes as transport vehicles. These compositions generally comprise one or more "cationic" lipids, including polyunsaturated neutral lipids (e.g., phospholipids), structural lipids (e.g., steroids), and/or polyethylene glycol-containing lipids (polymer conjugated lipids). Cationic lipids can be easily protonated and include amine-containing lipids.

However, the use of oligonucleotides in therapeutic settings currently faces two problems. First, free RNA is readily digested by nucleases in the plasma. Second, the ability of free RNA to enter intracellular compartments where relevant translational mechanisms exist is limited. Lipid nanoparticles formed from cationic lipids with other lipid components, such as neutral lipids, cholesterol, PEG, PEGylated lipids, and oligonucleotides, have been used to prevent RNA degradation in plasma and promote cellular uptake of oligonucleotides.

There is still a need for improved cationic lipids and lipid nanoparticles for delivery of oligonucleotides. Improved lipid nanoparticles will provide optimized drug delivery, protect nucleic acids from degradation and clearance in serum, are suitable for systemic or local delivery, and provide intracellular delivery of nucleic acids. In addition, these preferred lipid-nucleic acid particles should be well tolerated and provide a sufficient therapeutic index, such that patient treatment at an effective dose of the nucleic acid does not result in unacceptable toxicity and/or risk to the patient. The present invention provides these advantages.

SUMMARY OF THE INVENTION

The present invention provides novel cationic lipids that can be used for binding to other lipid components, such as neutral lipids, steroids, and polymer conjugated lipids, in order to form a nucleic acid mRNA lipid nanoparticle composition, a method of delivering one or more therapeutic and/or prophylactic agents to mammalian cells or organs and/or producing polypeptides in mammalian cells or organs. In addition to the novel lipids, the lipid nanoparticle compositions of the present invention may also comprise one or more cationic and/or ionizable amino lipids in a specific proportion, neutral lipids including polyunsaturated lipids, polymer conjugated lipids, steroids, and/or therapeutic and/or prophylactic agents.

DETAILED DESCRIPTION OF THE INVENTION

The present invention provides the following compounds and methods involving these compounds:

In a first aspect, the present invention relates to a compound of formula (I), (I)

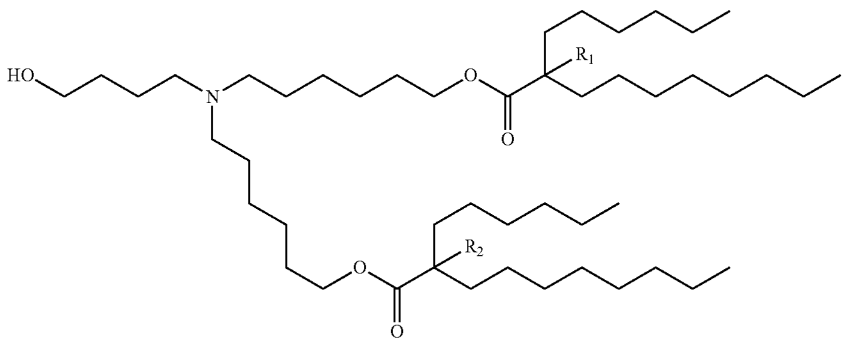

or a salt or isomer or an N-oxide thereof, wherein $R_1$ and $R_2$ are $C_{1-3}$ alkyl or hydrogen, but both are not hydrogen at the same time.
In certain embodiments, the compound of formula (I) has one of the structures shown below in Table 1.
TABLE 1
| Representative Compounds | |
|---|---|
| Number | Structure |
| 1 | 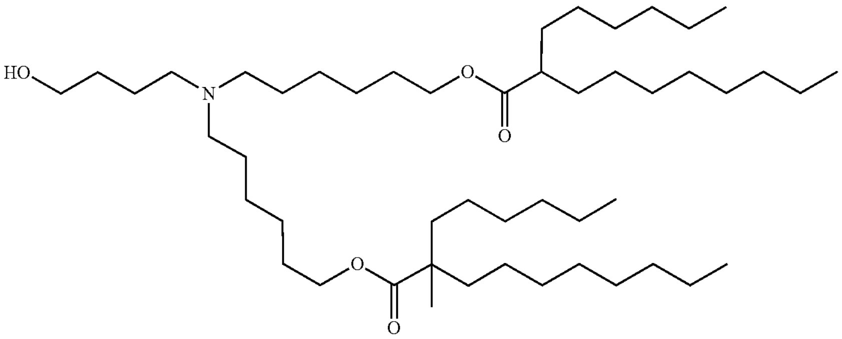 [SMILES: CCCCCCCCC(CCCCCC)C(=O)OCCCCCCN(CCCCO)CCCCCCOC(=O)C(C)(CCCCCC)CCCCCCCC] |
| 2 | 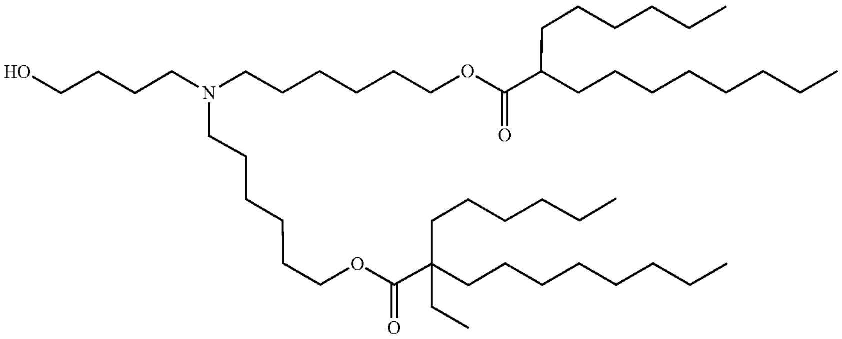 [SMILES: CCCCCCCCC(CCCCCC)C(=O)OCCCCCCN(CCCCO)CCCCCCOC(=O)C(CC)(CCCCCC)CCCCCCCC] |
| 3 | 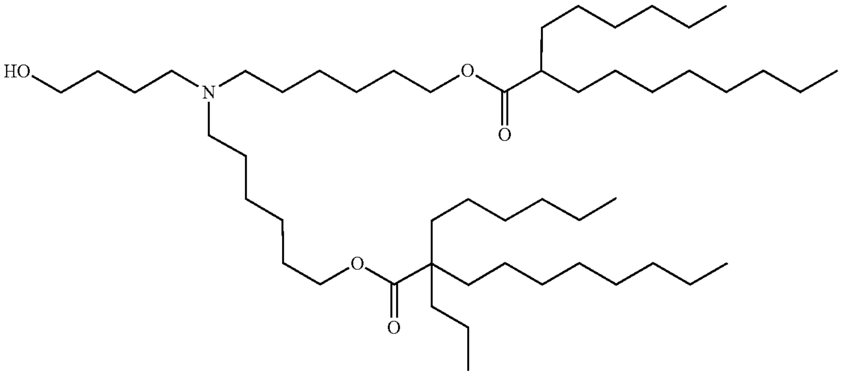 [SMILES: CCCCCCCCC(CCCCCC)C(=O)OCCCCCCN(CCCCO)CCCCCCOC(=O)C(CCC)(CCCCCC)CCCCCCCC] |
| 4 | 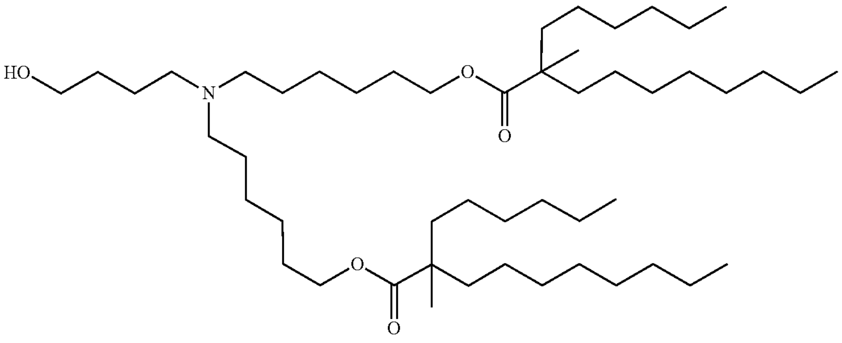 [SMILES: CCCCCCCCC(C)(CCCCCC)C(=O)OCCCCCCN(CCCCO)CCCCCCOC(=O)C(C)(CCCCCC)CCCCCCCC] |

TABLE 1-continued
| Representative Compounds | |
|---|---|
| Number | Structure |
| 5 | 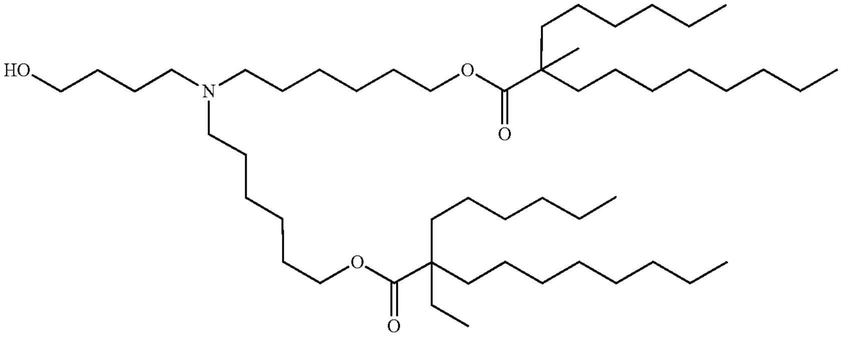 [SMILES: CCCCCCCCC(C)(CCCCCC)C(=O)OCCCCCCN(CCCCO)CCCCCCOC(=O)C(CC)(CCCCCC)CCCCCCCC] |
| 6 | 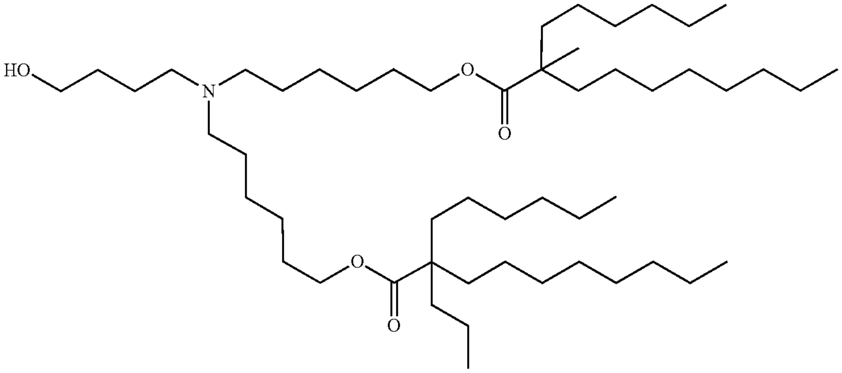 [SMILES: CCCCCCCCC(C)(CCCCCC)C(=O)OCCCCCCN(CCCCO)CCCCCCOC(=O)C(CCC)(CCCCCC)CCCCCCCC] |
| 7 | 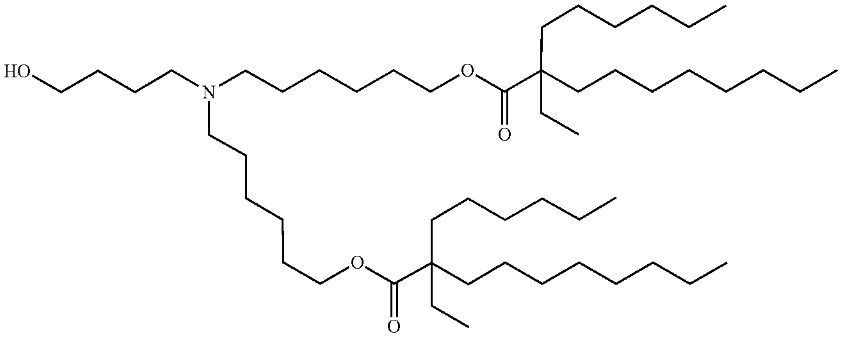 [SMILES: CCCCCCCCC(CC)(CCCCCC)C(=O)OCCCCCCN(CCCCO)CCCCCCOC(=O)C(CC)(CCCCCC)CCCCCCCC] |
| 8 | 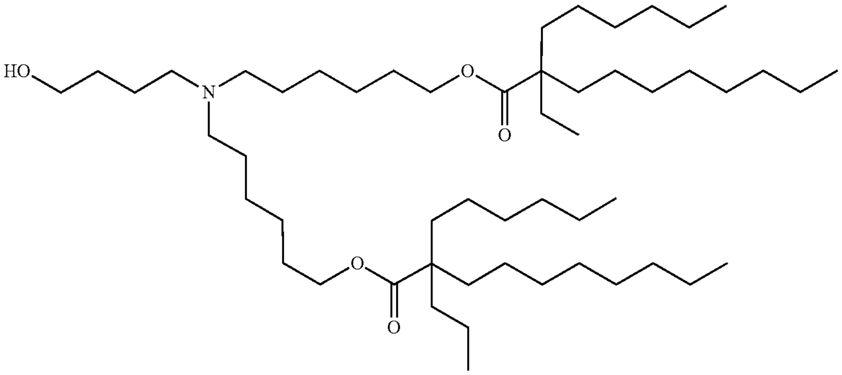 [SMILES: CCCCCCCCC(CC)(CCCCCC)C(=O)OCCCCCCN(CCCCO)CCCCCCOC(=O)C(CCC)(CCCCCC)CCCCCCCC] |

TABLE 1-continued

| Representative Compounds | |
|---|---|
| Number | Structure |
| 9 | 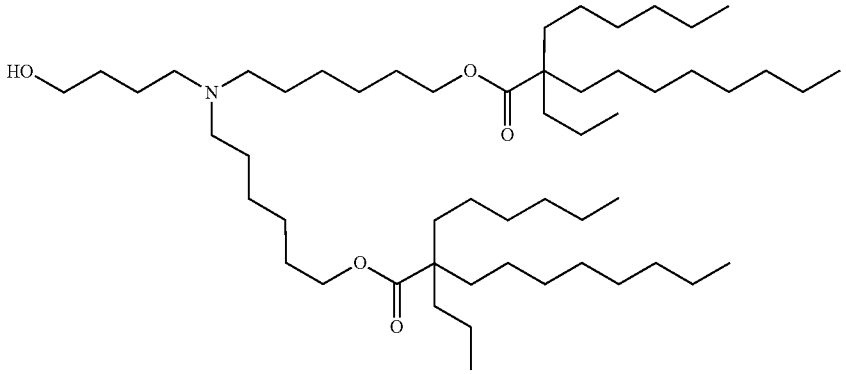 [SMILES: CCCCCCCCC(CCC)(CCCCCC)C(=O)OCCCCCCN(CCCCO)CCCCCCOC(=O)C(CCC)(CCCCCC)CCCCCCCC] |

In certain embodiments, a pharmaceutical composition including any one or more of the compounds of formula (I) and a therapeutic and/or prophylactic agent is provided.

In certain embodiments, a pharmaceutical composition including one or more of the compounds of formula (I) and a therapeutic and/or prophylactic agent is provided. In some embodiments, the pharmaceutical composition includes one of the compounds of formula (I), a therapeutic and/or prophylactic agent, and one or more excipients selected from neutral lipids, steroids, and polymer conjugated lipids. Other pharmaceutically acceptable excipients and/or carriers can also be included in various embodiments of the composition.

In certain embodiments, the neutral lipid is selected from the group consisting of 1,2-dipalmitoyl-sn-glycero-3-phosphocholine (DSPC), 1,2-dipalmitoyl-sn-glycero-3-phosphocholine (DPPC), 1,2-dimethoyl-sn-glycero-phosphocholine (DMPC), 1,2-dioleoyl-sn-glycero-3-phosphocholine (DOPC), 1-palmitoyl-2-oleoyl-sn-glycero-3-phosphocholine (POPC), 1,2-dioleoyl-sn-glycero-3-phosphoethanolamine (DOPE), sphingomyelin (SM), and mixtures thereof. In certain embodiments, the neutral lipid is DSPC.

In certain embodiments, the steroid is selected from the group consisting of cholesterol, fecal steroid, sitosterol, ergosterol, rapeseed sterol, soybean sterol, rapeseed sterol, tomatidine, ursolic acid, alpha-tocopherol, and mixtures thereof. In certain embodiments, the steroid is cholesterol.

In certain embodiments, the PEGylated lipid is 1,2-dimyristoyl-sn-glycerol methoxy polyethylene glycol (PEG-DMG)

In certain embodiments, the ratio of components in the pharmaceutical composition ranges from about 10 to about 60 mol % of the compound of formula (I), about 0 to about 30 mol % neutral lipid, about 10 to about 55 mol % steroid, and about 0 to about 10 mol % polymer conjugated lipids.

In certain embodiments, the therapeutic and/or prophylactic agents is a nucleic acid, wherein the nucleic acid is RNA selected from the group consisting of siRNA, aiRNA, miRNA, dsRNA, shRNA, mRNA. In certain embodiments, the RNA is selected from mRNA.

In other embodiments, the disclosure relates to a method of administering a therapeutic and/or prophylactic agent to a subject in need thereof comprising preparing or providing the pharmaceutical composition and administering the pharmaceutical composition to the subject.

For the purpose of administration, the compounds of formula (I) in combination with the therapeutic and/or prophylactic agent (typically in the form of lipid nanoparticles in combination with the therapeutic and/or prophylactic agent) are administered to the subject or are formulated into a pharmaceutical composition for administration to the subject. In some embodiments, the compound of formula (I) serves as active pharmaceutical ingredient for administration to the subject. The pharmaceutical composition includes a compound of formula (I) and one or more pharmaceutically acceptable carriers, diluents or excipients. The pharmaceutical compositions include the compound of formula (I) in an amount sufficient to effectively form lipid nanoparticles delivering the therapeutic and/or prophylactic agents. Those skilled in the art may readily determine suitable concentrations and doses for administration.

The administration of the pharmaceutical compositions may be carried out using any acceptable mode of administration with any agent for similar utility. The pharmaceutical compositions may be formulated as a solid, semi-solid, liquid, or gaseous formulation, such as tablets, capsules, powders, granules, ointments, solutions, suspensions, suppositories, injections, inhalers, gels, microspheres, and aerosols. Typical routes of administration include, but are not limited to, oral, topical, transdermal, inhalation, parenteral, sublingual, rectal, vaginal, and intranasal routes. The term parenteral as used herein includes subcutaneous, intravenous, intramuscular, intradermal, intrasternal, and infusion techniques. The pharmaceutical composition is formulated so as to allow the therapeutic and/or prophylactic agent contained therein to be bioavailable after administration of the pharmaceutical composition to the subject. The pharmaceutical composition can be administered to the subject in the form of one or more dosage units, such as a tablet, which may be a single dosage unit. In one embodiment, the pharmaceutical composition is administered as an aerosol from a container, which may contain multiple dosage units. Current methods of preparing these dosage forms are known, or are apparent to those skilled in the art. In any event, the composition to be administered contains a therapeutically effective amount of a compound of formula (I), or a pharmaceutically acceptable salt thereof, in order to treat a relevant disease or condition.

The pharmaceutical composition may be in the form of a solid or liquid. In one embodiment, the carrier is in the particle form while the pharmaceutical composition is in tablet or powder form. In one embodiment, the carrier is in the form of a liquid when the pharmaceutical composition is a liquid, such as an oral syrup or an injectable liquid. In one embodiment, the pharmaceutical composition is an aerosol suitable for administration by inhalation.

When intended for oral administration, the pharmaceutical composition is preferably in solid or liquid form, such as a solid, semi-solid, semi-liquid, suspension, or gel form.

As a solid pharmaceutical composition for oral administration, the pharmaceutical composition may be provided in the form of a powder, granules, compressed tablets, pills, capsules, chewing gums, flakes, and the like. Such solid compositions will generally contain one or more inert diluents or edible carriers. In addition, the pharmaceutical composition may further include one or more of the following excipients: adhesives, such as gelatin, cellulose, and the like; excipients, such as lactose and the like; disintegrants, such as alginic acid and the like; lubricants, such as magnesium stearate and the like; glidants, such as silica gel and the like; sweeteners such as sucrose, saccharin, and the like; flavoring, such as peppermint and the like; and colorants.

When the pharmaceutical composition is a capsule, it may contain a liquid carrier, such as polyethylene glycol or oil.

The pharmaceutical composition may be in liquid form, such as a syrup, solution, emulsion, or suspension. As two examples, liquids may be used for oral administration or for injection delivery. When intended for oral administration, the pharmaceutical compositions may include, in addition to the compound of formula (I), one or more excipients selected from the group consisting of sweeteners, preservatives, dyes/colorants, and enhancers. In pharmaceutical compositions administered by injection, the pharmaceutical compositions may include, in addition to the compound of formula (I) and the therapeutic and/or prophylactic agent, one or more of a surfactant, a preservative, a wetting agent, a dispersant, a suspension agent, a buffer, a stabilizer, and an isotonic agent.

The liquid pharmaceutical compositions, whether in solution, suspension or other similar form, may comprise one or more of the following adjuvants: sterile diluents such as water for injection, aqueous brine solution, preferably normal saline, Ringer's solution, and isotonic sodium chloride; non-volatile oils such as synthetic monoglycerides or diglycerides, polyethylene glycols, glycerol, propylene glycols, or other solvents that can be used as dissolving or suspending media; antimicrobial agents, such as methylparaben; antioxidants such as ascorbic acid or sodium bisulfite; chelating agents such as ethylene diamine tetraacetic acid; buffering agents such as acetate, citrate, or phosphate; reagents for adjusting tonicity, such as sodium chloride or glucose; and reagents used as cryoprotectants, such as sucrose or trehalose. Parenteral preparations may be packaged in glass or plastic ampoules, disposable syringes, or multi-dose vials. Saline is a preferred adjuvant. The injectable pharmaceutical composition is preferably sterile.

The pharmaceutical composition of the invention may consist of dosage units that can be administered as an aerosol. The term aerosol, as used herein, denotes a variety of systems from systems of colloidal nature to systems consisting of pressurized packaging. In such dosage unit the pharmaceutical composition may be delivered by liquefied or compressed gas, or by a suitable pump system that disperses the pharmaceutical composition. Aerosols of pharmaceutical compositions may be delivered as monophasic, biphasic, or triphasic systems for delivery of active component. Aerosol delivery systems includes the necessary containers, activators, valves, sub-containers, and the like, which together can form a kit. Preferred aerosol dosage units can be determined by those skilled in the art without excessive experimentation.

The pharmaceutical compositions can be prepared by methods well known in the pharmaceutical arts. Pharmaceutical compositions intended for administration by injection may be prepared by combining the lipid nanoparticles with sterile distilled water or other carriers to provide a solution or suspension. A surfactant may be included in the formulation to facilitate the formation of a homogeneous solution or suspension. A surfactant is a compound that non-covalently interacts with the compound of formula (I) in order to facilitate dissolution or provide a homogeneous suspension of the pharmaceutical composition in an aqueous delivery system.

The pharmaceutical composition is administered in a therapeutically effective amount that will vary according to a variety of factors, including, but not limited to, the activity of the therapeutic agent; the metabolic stability and duration of action of therapeutic agents; the age, weight, general health status, sex, and diet of the subject; the mode and time of administration; the excretion rate of the therapeutic agent; other drugs administered in combination with the therapeutic agent; and the seriousness of the disorder being treated.

The pharmaceutical compositions may also be administered concurrently, before, or after the administration of one or more other therapeutic agents. Such combination therapies include administering a single dose of the therapeutic and/or prophylactic agent and the compound of formula (I) in combination with one or more additional active agents as a single dosage form, and administering the therapeutic and/or prophylactic agent and the compound of formula (I) and the one or more additional active agents as separate dosage forms. For example, pharmaceutical compositions containing the therapeutic and/or prophylactic agent and the compound of formula (I) in combination with other active agents may be administered to a subject together as a single oral dosage form (e.g., tablets or capsules), or each active agent may be administered in different oral dosage forms. When different dosage forms are used, the therapeutic and/or prophylactic agent and the compound of formula (I) and the one or more additional active agents may be administered at substantially the same time, or sequentially at staggered times. It should be understood that combination therapies include all of these dosing regimens.

The cationic lipid compounds of formula (I) have advantageous physicochemical properties, including more suitable pKa and better chemical stability, that allow for producing mRNA liposome compositions that provide efficient binding and delivery of nucleic acid to cells. The cationic lipid compounds of formula (I) also have a chemical structure that exhibits good stability, which facilitates synthesis and development as a pharmaceutical composition.

Methods for the preparation of the above compounds and pharmaceutical compositions are described below, and/or are known in the art.

Those skilled in the art will recognize that in the methods described herein, the functional groups of intermediate compounds used to make the compounds of formula (I) may need to be protected by suitable protecting groups. Such functional groups include, but are not limited to, hydroxyl, amino and carboxylic acid groups. Suitable protecting groups for hydroxyl groups include trialkylsilyl or diarylalkylsilyl, tetrahydrofuranyl, benzyl, and the like. Suitable protecting groups for amino groups include tert-butoxycarbonyl, benzyloxycarbonyl, and the like. Suitable protecting groups for carboxylic acids include hydrocarbon, aryl, or arene esters, and the like. Protective groups may be added or removed in accordance with standard techniques known to those of ordinary skill in the art.

Those of ordinary skill in the art will also recognize that while protected derivatives of the therapeutic and/or prophylactic compounds used in the methods of the invention may not thereby have pharmaceutical activity, they may be administered to mammals and subsequently metabolized in vivo to form pharmacologically active compounds. Such derivatives can therefore be described as "prodrugs". Prodrugs of the compounds of the invention are therefore included within the scope of the invention.

In addition, all therapeutic and/or prophylactic compounds present in the form of a free base or free acid may be converted to pharmaceutically acceptable salts thereof by treatment with suitable inorganic or organic base or acid, according to methods known to those skilled in the art. Salts of the compounds of the invention can be converted by standard techniques to their free base or acid form.

EXAMPLES

The following embodiments are provided for illustrative purposes and do not limit the scope of the invention.

In the following examples, all solvents and reagents used were commercially available and used as is, unless otherwise indicated.

The procedure described below can be used for the synthesis of related compounds.

The following abbreviations are used herein:

EDC·HCl: 1-ethyl-3-(3-dimethylaminopropyl) carbodiimide hydrochloride

DCM: dichloromethane

DMAP: 4-Dimethylaminopyridine

DIEA: N, N-diisopropylethylamine

THF: tetrahydrofuran

Example 1

Representative Route.

Synthesis of Compound 7

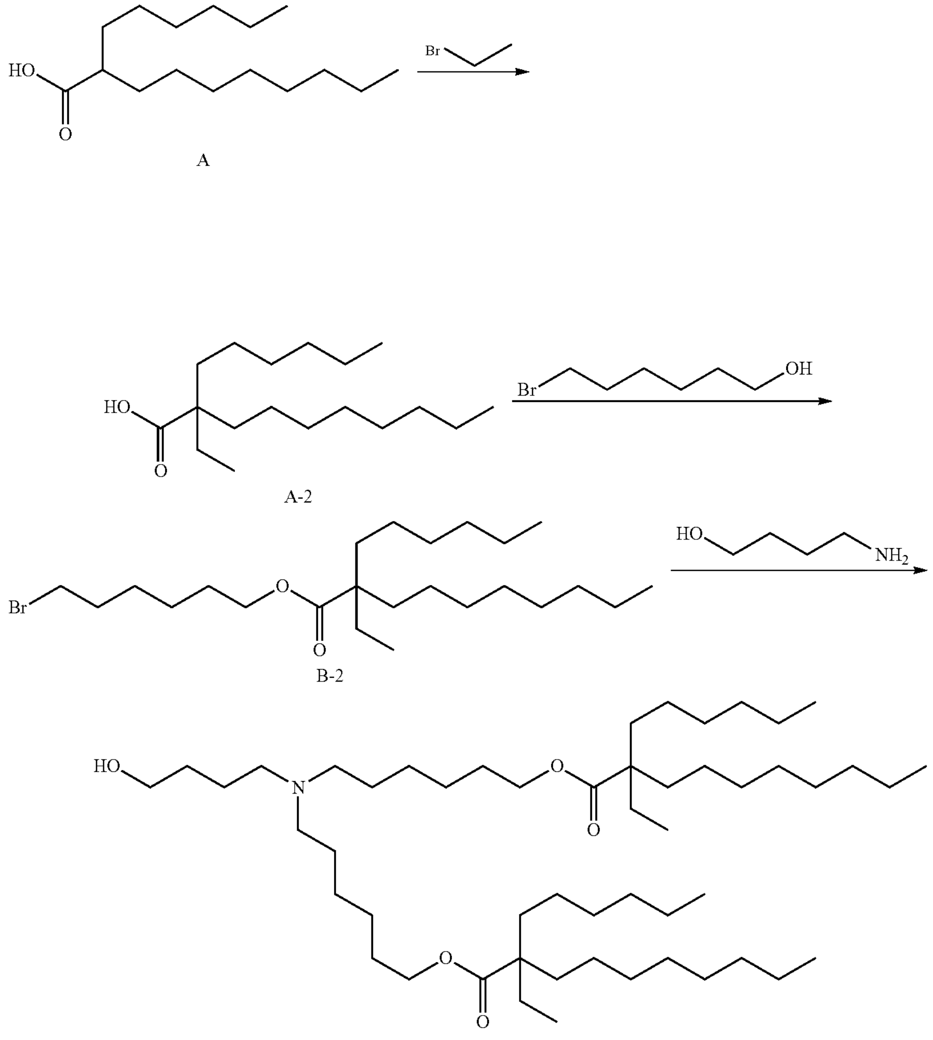

A

A-2

B-2

7

1) Synthesis of Compound A-2

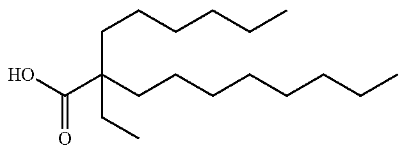 [SMILES: CCCCCCCCC(CC)(CCCCCC)C(=O)O]

Chemical Formula: $C_{18}H_{36}O_2$

Molecular Weight: 284.48

Diisopropylamine (3 mL, 21.4 mmol) was dissolved in 10 mL of THF. The mixture was then cooled to-78° C., and n-butyl lithium solution (2.5 M n-hexane solution, 7.7 mL, 19.3 mmol) was added dropwise to the mixture. After the solution was heated slowly to 0° C., 2-hexyldecanoic acid (4.49 g, 17.5 mmol, in 20 mL THF) was added dropwise to the solution, which was then stirred at room temperature for 30 minutes. 1-bromoethane (2.10 g, 19.3 mmol) was added. Then the resulting solution was heated to 30° C. and allowed to react for 8 hours. The reaction was then quenched with dilute hydrochloric acid and ethyl acetate was added. The organic layer was separated, dried with anhydrous sodium sulfate, and finally concentrated in vacuo. The resulting residue was purified by silica gel column (ethyl acetate/n-hexane) to obtain Compound A-2 (1.5 g, 5.3 mmol) in 30% yield.

2) Synthesis of Compound B-2

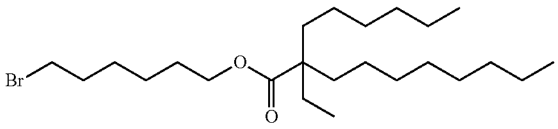 [SMILES: CCCCCCCCC(CC)(CCCCCC)C(=O)OCCCCCCBr]

Chemical Formula: $C_{24}H_{47}BrO_2$

Molecular Weight: 447.54

To a mixture of Compound A-2 (1.50 g, 5.3 mmol) and 6-bromohexanol (1.20 g, 6.6 mmol) in DCM (20 mL), EDC·HCl (1.26 g, 6.6 mmol), DMAP (0.06 g, 0.5 mmol), and DIEA (2.05 g, 15.9 mmol) were sequentially added and allowed to react at room temperature for 24 hours. After being washed with saturated sodium bicarbonate solution and dilute hydrochloric acid successively, the organic layer was separated and then dried using anhydrous sodium sulfate and concentrated in vacuo. The residue was purified by a silica gel column (ethyl acetate/n-hexane) to obtain the Compound B-2 (1.5 g, 3.4 mmol) in 64% yield.

3) Synthesis of Compound 7

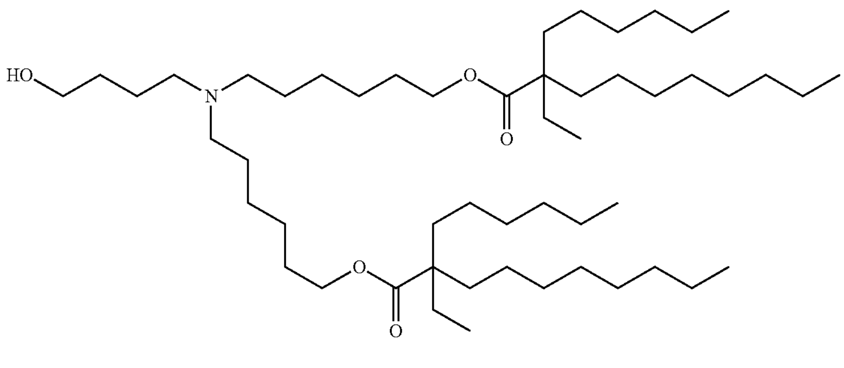 [SMILES: CCCCCCCCC(CC)(CCCCCC)C(=O)OCCCCCCN(CCCCO)CCCCCCOC(=O)C(CC)(CCCCCC)CCCCCCCC]

Chemical Formula: $C_{52}H_{103}NO_5$
Molecular Weight: 822.40

To a mixture of Compound B-2 (1.50 g, 3.4 mmol) and ethanol, 4-amino-1-butanol (0.13 g, 1.5 mmol) and DIEA (1.03 g, 10.2 mmol) were added and allowed to react at 60° C. for 32 hours. After being concentrated under vacuum, ethyl acetate and water were added. The organic layer was separated, dried with anhydrous sodium sulfate, and further concentrated in vacuo. The resulting residue was purified by a silica gel column (ammonia/methanol/DCM) to obtain Compound 7 (0.9 g, 1.1 mmol) in 73% yield.

$C_{52}H_{103}NO_5$, Ms m/z: [M+H$^+$] 823; $^1$H-NMR (300 MHz, $CDCl_3$)δ: ppm 4.10 (4H, t), 3.49 (2H, t), 3.05 (6H, t), 1.76~1.41 (18H, m), 1.38~1.17 (54H, m), 0.87 (18H, m).

Example 2

Compound 1:

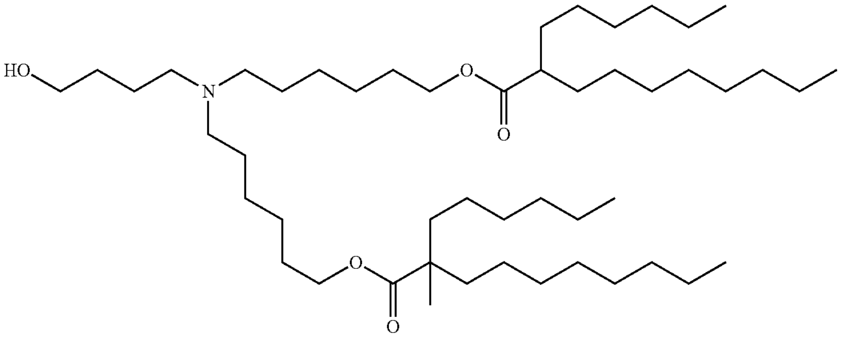

Chemical Formula: $C_{49}H_{97}NO_5$
Molecular Weight: 780.32

Compound 1 can be synthesized according to the representative route described in Example 1.

$C_{49}H_{97}NO_5$, Ms m/z: [M+H$^+$ ]781; $^1$H-NMR (300 MHz, $CDCl_3$) δ: ppm 4.08 (4H, t), 3.47 (2H, t), 3.03 (6H, t), 2.11 (1H, m), 1.74~1.48 (14H, m), 1.43~1.15 (57H, m), 0.88 (12H, m).

Example 3

Compound 2:

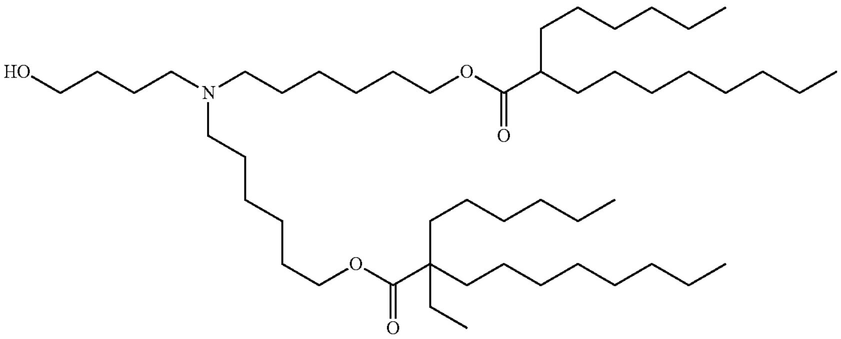 [SMILES: CCCCCCCCC(CCCCCC)C(=O)OCCCCCCN(CCCCO)CCCCCCOC(=O)C(CC)(CCCCCC)CCCCCCCC]

Chemical Formula: $C_{50}H_{99}NO_5$

Molecular Weight: 794.34

Compound 2 can be synthesized according to the representative route described in Example 1.

$C_{50}H_{99}NO_5$, Ms m/z: $[M+H^+]$ 795; $^1$H-NMR (300 MHz, $CDCl_3$) δ: ppm 4.09 (4H, t), 3.48 (2H, t), 3.04 (6H, t), 2.11 (1H, m), 1.74~1.48 (16H, m), 1.43~1.15 (54H, m), 0.88 (15H, m).

Example 4

Compound 3:

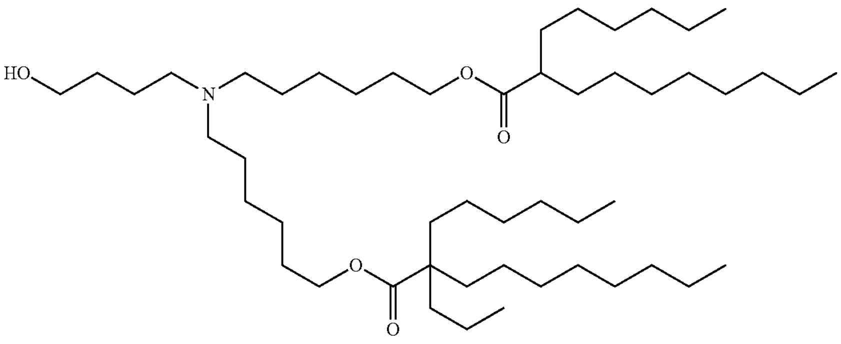

Chemical Formula: $C_{51}H_{101}NO_5$

Molecular Weight: 808.37

Compound 3 can be synthesized according to a representative route described in Example 1.

$C_{51}H_{101}NO_5$, Ms m/z: $[M+H^+]$ 809; $^1$H-NMR (300 MHz, $CDCl_3$) δ: ppm 4.06 (4H, t), 3.46 (2H, t), 3.02 (6H, t), 2.11 (1H, m), 1.78~1.45 (16H, m), 1.43~1.15 (56H, m), 0.86 (15H, m).

Example 5

Compound 4:

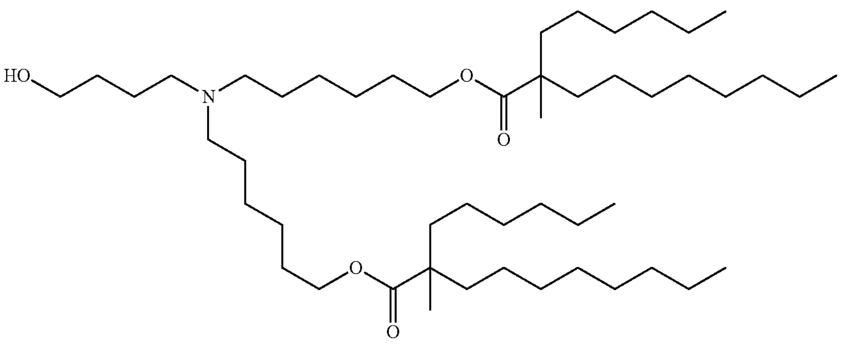 [SMILES: CCCCCCCCC(C)(CCCCCC)C(=O)OCCCCCCN(CCCCO)CCCCCCOC(=O)C(C)(CCCCCC)CCCCCCCC]

Chemical Formula: $C_{50}H_{99}NO_5$
Molecular Weight: 794.34

Compound 4 can be synthesized according to the representative route described in Example 1.

$C_{50}H_{99}NO_5$, Ms m/z: [M+H$^+$] 795; $^1$H-NMR (300 MHz, $CDCl_3$) δ: ppm 4.11 (4H, t), 3.46 (2H, t), 3.02 (6H, t), 1.70~1.50 (14H, m), 1.48~1.13 (60H, m), 0.88 (12H, m).

Example 6

Compound 5:

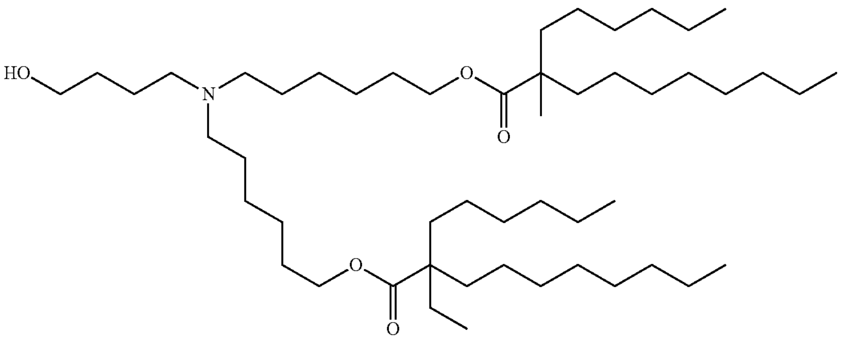 [SMILES: CCCCCCCCC(C)(CCCCCC)C(=O)OCCCCCCN(CCCCO)CCCCCCOC(=O)C(CC)(CCCCCC)CCCCCCCC]

Chemical Formula: $C_{51}H_{101}NO_5$
Molecular Weight: 808.37

Compound 5 can be synthesized according to the representative route described in Example 1.

$C_{31}H_{101}NO_5$, Ms m/z: [M+H$^+$] 809; $^1$H-NMR (300 MHz, $CDCl_3$) δ: ppm 4.11 (4H, t), 3.46 (2H, t), 3.02 (6H, t), 1.70~1.48 (16H, m), 1.47~1.13 (57H, m), 0.88 (15H, m).

Example 7

Compound 6:

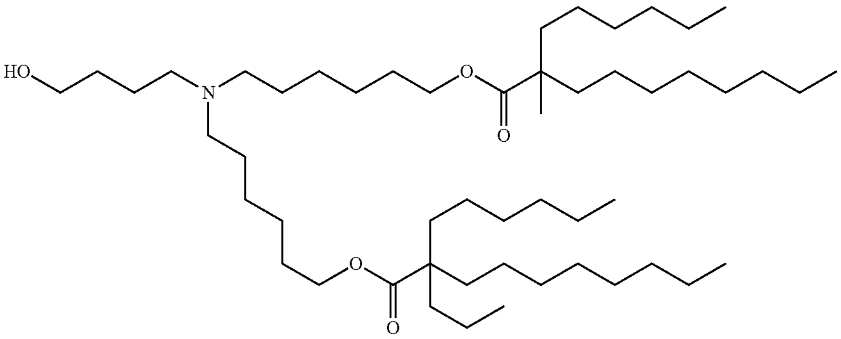 [SMILES: CCCCCCCCC(C)(CCCCCC)C(=O)OCCCCCCN(CCCCO)CCCCCCOC(=O)C(CCC)(CCCCCC)CCCCCCCC]

Chemical Formula: $C_{52}H_{103}NO_5$
Molecular Weight: 822.40

Compound 6 can be synthesized according to the representative route described in Example 1.

$C_{52}H_{103}NO_5$, Ms m/z: [M+H$^+$] 823; $^1$H-NMR (300 MHz, $CDCl_3$) δ: ppm 4.10 (4H, t), 3.45 (2H, t), 3.03 (6H, t), 1.73~1.48 (16H, m), 1.47~1.15 (59H, m), 0.88 (15H, m).

Example 8

Compound 8:

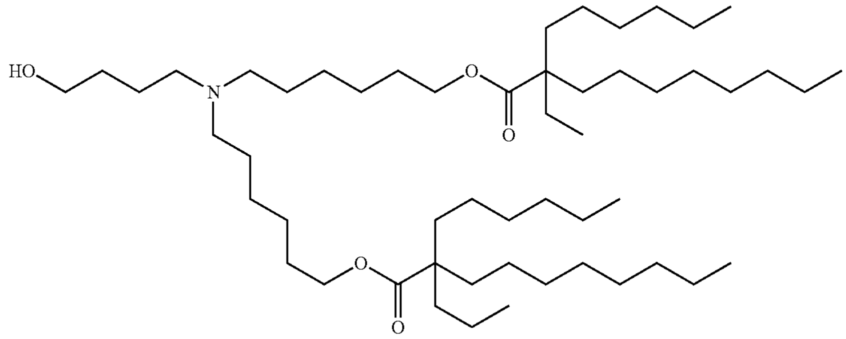 [SMILES: CCCCCCCCC(CC)(CCCCCC)C(=O)OCCCCCCN(CCCCO)CCCCCCOC(=O)C(CCC)(CCCCCC)CCCCCCCC]

Chemical Formula: $C_{53}H_{105}NO_5$
Molecular Weight: 836.43

Compound 8 can be synthesized according to the representative route described in Example 1.

$C_{53}H_{105}NO_5$, Ms m/z: [M+H$^+$] 837; $^1$H-NMR (300 MHz, $CDCl_3$) δ: ppm 4.07 (4H, t), 3.47 (2H, t), 3.01 (6H, t), 1.69~1.47 (18H, m), 1.45~1.13 (56H, m), 0.87 (18H, m).

Example 9

Compound 9:

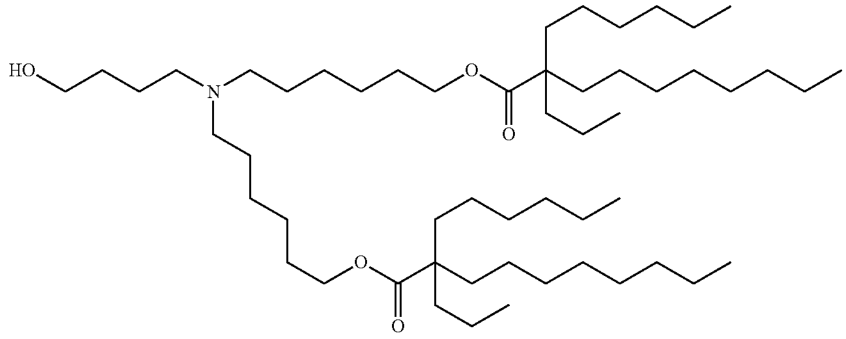 [SMILES: CCCCCCCCC(CCC)(CCCCCC)C(=O)OCCCCCCN(CCCCO)CCCCCCOC(=O)C(CCC)(CCCCCC)CCCCCCCC]

Chemical Formula: $C_{54}H_{107}NO_5$
Molecular Weight: 850.45

Compound 9 can be synthesized according to the representative route described in Example 1.

$C_{54}H_{107}NO_5$, Ms m/z: [M+H$^+$] 851; $^1$H-NMR (300 MHz, $CDCl_3$) δ: ppm 4.06 (4H, t), 3.47 (2H, t), 3.01 (6H, t), 1.65~1.48 (18H, m), 1.47~1.15 (58H, m), 0.88 (18H, m).

Example 10

Luciferase mRNA In Vivo Evaluation Using Lipid Nanoparticle Compositions.

Cationic lipids, DSPC, cholesterol, and PEG-lipids were dissolved in ethanol in molar ratios of 50:10:38:2 or 48:10:40:2. Lipid nanoparticles (LNPs) were prepared in a ratio of total lipid to mRNA by weight of about 10:1 to 30:1. Briefly, mRNA was diluted to 0.15 mg/ml in 10 to 50 ml of citrate buffer (pH=4). Using a syringe pump, an ethanolic solution of lipids was mixed with an aqueous mRNA solution in a ratio of approximately 1:5 to 1:3 by volume at a total flow rate of over 10 ml/min. Ethanol was then removed and the external buffer was replaced by dialysis-class PBS. Finally, the lipid nanoparticles were filtered through a sterile filter with a pore size of 0.2 um. The particle size of the lipid nanoparticles was approximately 65-105 nm in diameter and, in some cases, approximately 75-100 nm in diameter, determined by quasi-elastic light scattering using Malvern Zetasizer Nano ZS.

According to the guidelines set by the State Scientific and Technological Commission of The People's Republic of China, female C57BL/6 mice aged 6-8 weeks and CD-1 mice aged 8-10 weeks were used to perform the study. Various doses of mRNA lipid nanoparticles were administered by intravenous injection and the animals were euthanized at specific time points (e.g., 5 hours) post-administration. The liver and spleen were collected, weighed, immediately frozen in liquid nitrogen, and stored at −80° C. until being used for analysis.

For the liver, approximately 50 mg of liver tissue was cut and placed in 2 mL FastPrep tubes (MP Biomedicals, Solon OH) for analysis. ¼" ceramic beads (MP Biomedicals) and 500 μL of room temperature Glo Lysis Buffer-GLB (Promega, Madison WI) were then added to each tube. The liver tissue was then homogenized for 15 seconds at a speed of 2×6.0 m/s using a FastPrep24 instrument (MP Biomedicals). The homogenates were incubated at room temperature for 5 minutes, then diluted with GLB in a ratio of 1:4, and finally evaluated using the SteadyGlo luciferase assay system (Promega). Specifically, 50 μL of diluted tissue homogenate was mixed with 50 μL of SteadyGlo substrate. The mixture was shaken for 10 seconds, then incubated at room temperature for 5 minutes, and subsequently quantified using a SpectraMAX_L chemiluminescent plate reader (Meigu Molecular Instrument (Shanghai) Co., Ltd.). The amount of protein was measured by using the BCA Protein Quantitation Kit (Shanghai Colorless Medical Technology Co., Ltd.). Relative luminescence units (RLU) were normalized to the total ug of the measured protein. To convert RLU into μg luciferase, a standard curve was generated using QuantiLum recombinant luciferase (Promega).

FLuc mRNA (L-6107) from Trilink Biotechnologies, which was originally isolated from fireflies (*Photinus pyralis*), will express luciferase protein. Fluc is commonly used in mammalian cell cultures to measure gene expression and cell viability. It emits biological light in the presence of the substrate luciferin. This capped and polyadenylated mRNA was completely replaced by 5-methylcytidine and pseudouridine.

Example 11

Determination of the PKa of the Prepared Lipids.

The pKa of the formulated cationic lipid correlates with the effectiveness of the LNP for nucleic acid delivery. The preferred pKa range is from 5 to 7. The pKa of each cationic lipid was determined in lipid nanoparticles using an analysis based on the fluorescence of 2-(p-toluidine)-6-naphthalenesulfonic acid (TNS). Lipid nanoparticles containing cationic lipids/DSPC/cholesterol/PEG lipids (50/10/38/2 mol %) at a concentration of 0.4 mM total lipid in PBS were prepared using an ordered method as described in Example 10. TNS was prepared as a 100 μM stock solution in distilled water. The vesicles were diluted to contain 24 uM lipid in a 2 mL buffer solution containing 10 mM HEPES, 10 mM MES, 10 mM acetic acid, and 130 mM NaCl, pH 2.5-11. Aliquots of 100 μM TNS stock solution were added to bring the final concentration to 1 uM. After vortex mixing, fluorescence intensity was measured in an SLM Aminco Series 2 luminescence spectrophotometer at room temperature using excitation and emission wavelengths of 321 nm and 445 nm. Fluorescence data were analyzed using a s-shaped curve fitting and pKa was determined by measuring the pH that produced half-maximal fluorescence intensity.

Example 12

Determination of the Efficacy of Lipid Nanoparticle Formulations Containing Various Cationic Lipids Using Rodent Models of In Vivo Luciferase mRNA Expression.

For comparison purposes, these lipids were also used to formulate lipid nanoparticles containing FLuc mRNA (L-6107) using an ordered mixing method, as described in Example 10. Lipid nanoparticles were formulated with the following molar ratio: 50% cationic lipid/10% distearylphosphatidylcholine (DSPC)/38% cholesterol/2% PEG lipid ("PEG-DMG", i.e., (1-(monomethoxy-polyethylene glycol)-2,3-dimyristoylglycerol, average PEG molecular weight 2000). As described in Example 10, relative activity was determined by measuring luciferase expression in the liver 5 hours after administration via tail vein injection. The activity was compared at doses of 0.3 and 1.0 mg mRNA/kg and expressed as ng luciferase/g liver measured 5 hours after administration as described in Example 10. The results of Examples 10 and 11 are shown in Table 2.

TABLE 2

Comparison of lipids with mRNA exhibiting activity

| Compound | pKa | Liver Luc @ 0.3 mg/kg dose | Liver Luc @ 1.0 mg/kg dose | Structure |
|---|---|---|---|---|
| 1 | 6.25 | 1424 ± 265 | 10318 ± 1304 | 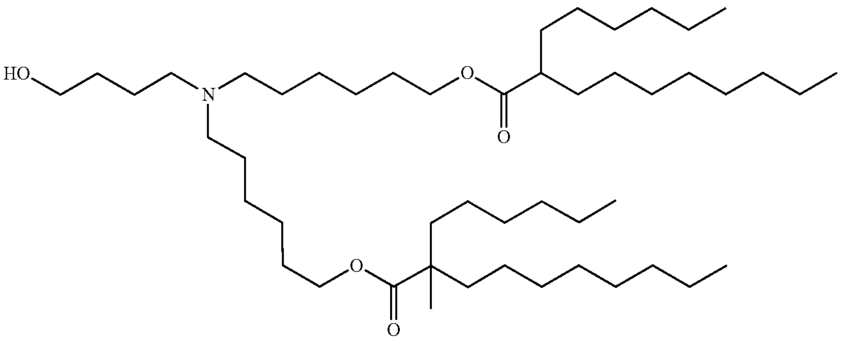 [SMILES: CCCCCCCCC(CCCCCC)C(=O)OCCCCCCN(CCCCO)CCCCCCOC(=O)C(C)(CCCCCC)CCCCCCCC] |

TABLE 2-continued
Comparison of lipids with mRNA exhibiting activity
| Compound | pKa | Liver Luc @ 0.3 mg/kg dose | Liver Luc @ 1.0 mg/kg dose | Structure |
|---|---|---|---|---|
| 2 | 5.91 | 1469 ± 294 | 10671 ± 1912 | 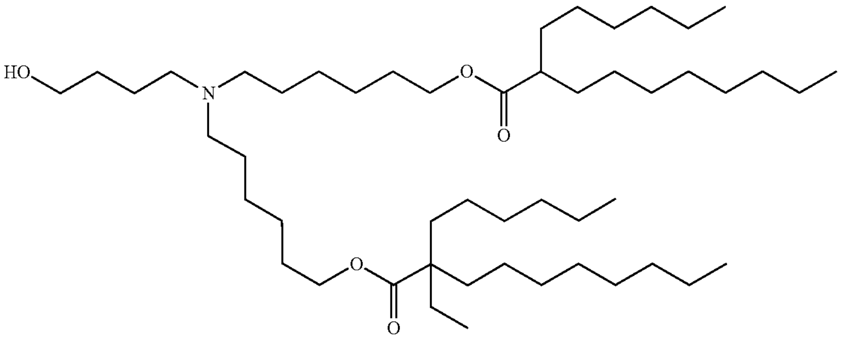 [SMILES: CCCCCCCCC(CCCCCC)C(=O)OCCCCCCN(CCCCO)CCCCCCOC(=O)C(CC)(CCCCCC)CCCCCCCC] |
| 3 | 6.22 | 961 ± 469 | 6917 ± 642 | 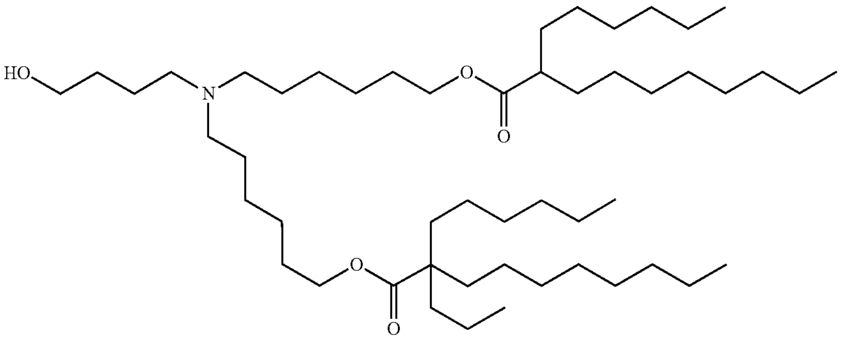 [SMILES: CCCCCCCCC(CCCCCC)C(=O)OCCCCCCN(CCCCO)CCCCCCOC(=O)C(CCC)(CCCCCC)CCCCCCCC] |
| 4 | 6.12 | 1179 ± 362 | 8630 ± 824 | 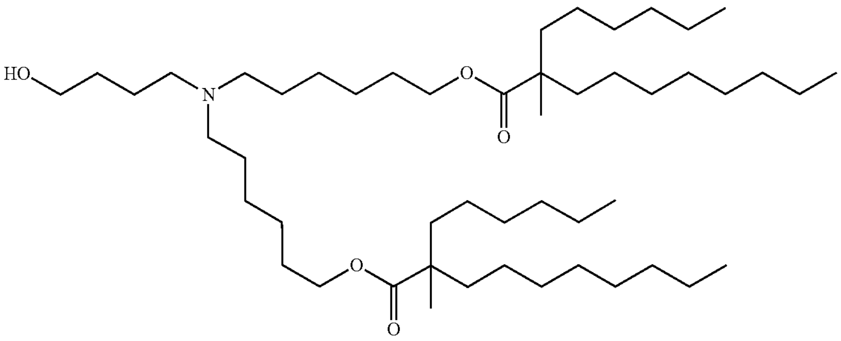 [SMILES: CCCCCCCCC(C)(CCCCCC)C(=O)OCCCCCCN(CCCCO)CCCCCCOC(=O)C(C)(CCCCCC)CCCCCCCC] |
| 5 | 5.89 | 1424 ± 289 | 10372 ± 2096 | 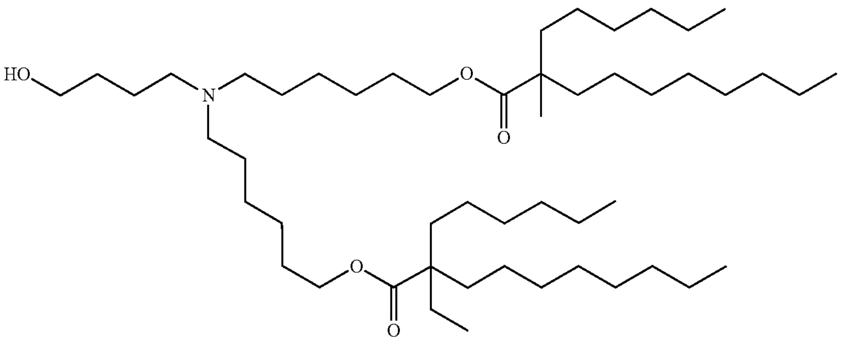 [SMILES: CCCCCCCCC(C)(CCCCCC)C(=O)OCCCCCCN(CCCCO)CCCCCCOC(=O)C(CC)(CCCCCC)CCCCCCCC] |

TABLE 2-continued
Comparison of lipids with mRNA exhibiting activity
| Compound | pKa | Liver Luc @ 0.3 mg/kg dose | Liver Luc @ 1.0 mg/kg dose | Structure |
|---|---|---|---|---|
| 6 | 6.13 | 1628 ± 432 | 11753 ± 2598 | 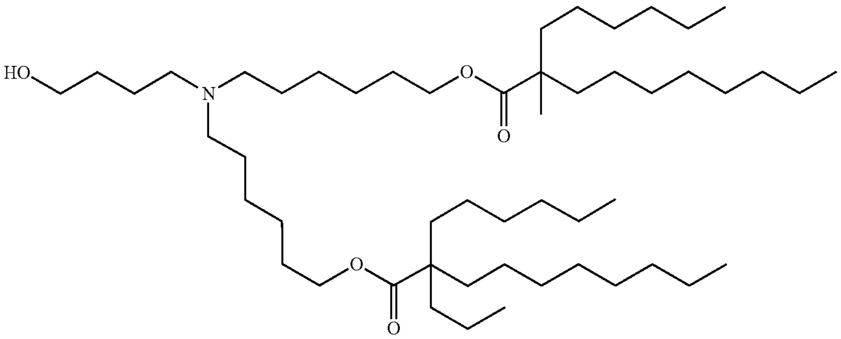 [SMILES: CCCCCCCCC(C)(CCCCCC)C(=O)OCCCCCCN(CCCCO)CCCCCCOC(=O)C(CCC)(CCCCCC)CCCCCCCC] |
| 7 | 6.08 | 1218 ± 359 | 8914 ± 1487 | 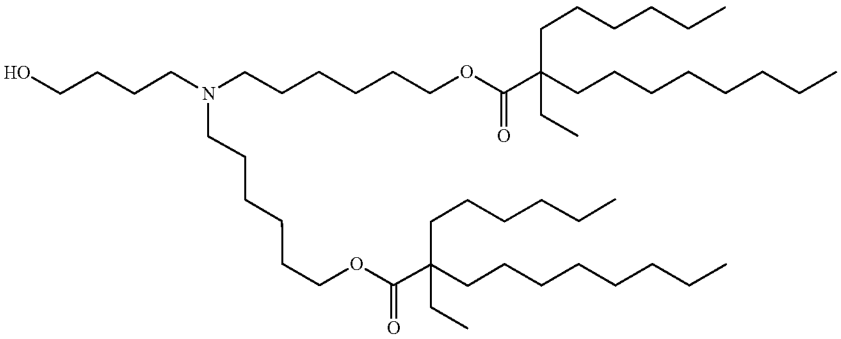 [SMILES: CCCCCCCCC(CC)(CCCCCC)C(=O)OCCCCCCN(CCCCO)CCCCCCOC(=O)C(CC)(CCCCCC)CCCCCCCC] |
| 8 | 5.98 | 985 ± 625 | 7188 ± 942 | 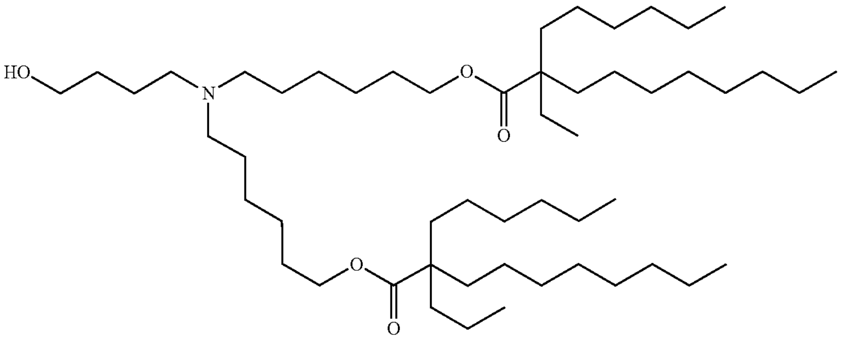 [SMILES: CCCCCCCCC(CC)(CCCCCC)C(=O)OCCCCCCN(CCCCO)CCCCCCOC(=O)C(CCC)(CCCCCC)CCCCCCCC] |
| 9 | 6.05 | 1138 ± 265 | 8443 ± 1045 | 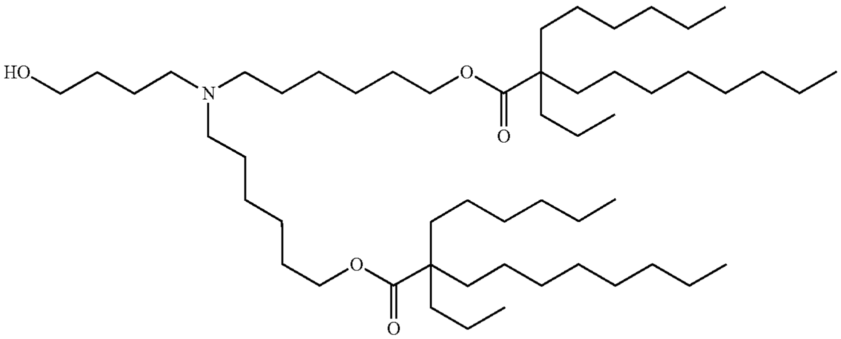 [SMILES: CCCCCCCCC(CCC)(CCCCCC)C(=O)OCCCCCCN(CCCCO)CCCCCCOC(=O)C(CCC)(CCCCCC)CCCCCCCC] |

Each of the technical features of the above described embodiments may be combined in any way, and all possible combinations of each of the technical features in the above embodiments are not described in order to make the description concise, however, as long as there is no contradiction in the combination of these technical features, it should be considered within the scope of this specification.

The above described embodiments express only several embodiments of the invention, which are described in detail, but should be understood as not limiting the scope of the disclosed invention. It should be noted that for those of ordinary skill in the art, a number of improvements may also be made without departing from the inventive concept, all of which fall within the scope of protection of the invention.

What is claimed is:

1. A compound of structure (I):

(I)

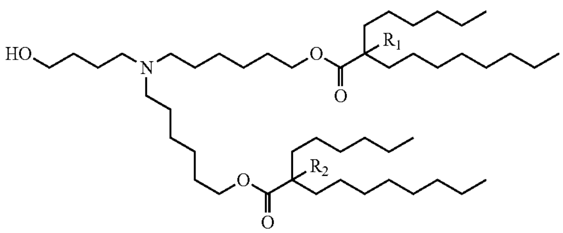

or a salt, isomer or an N-oxide thereof, wherein $R_1$, $R_2$ are independently $C_{1-3}$ alkyl or hydrogen, and wherein R1 and R2 cannot simultaneously be hydrogen.

2. The compound of claim 1, wherein the $C_{1-3}$ alkyl group is a linear alkane.

3. The compound of claim 2, wherein the $C_{1-3}$ alkyl group is methyl, ethyl, n-propyl.

4. A composition comprising the compound of claim 1 and a therapeutic and/or prophylactic agent.

5. The composition of claim 4, further comprising one or more excipients selected from the group consisting of neutral lipids, steroids, and polymer conjugated lipids.

6. The composition of claim 4, further comprising one or more excipients selected from the group consisting of:

(a) a neutral lipid is selected from the group consisting of 1,2-distearoyl-sn-glycero-3-phosphocholine (DSPC), 1,2-dipalmitoyl-sn-glycero-3-phosphocholine (DPPC), 1,2-dimethoyl-sn-glycero-phosphocholine (DMPC), 1,2-dioleoyl-sn-glycero-3-phosphocholine (DOPC), 1-palmitoyl-2-oleoyl-sn-glycero-3-phosphocholine (POPC), 1,2-dioleoyl-sn-glycero-3-phosphoethanolamine (DOPE), sphingomyelin (SM), and combinations thereof;

(b) a steroid selected from the group consisting of cholesterol, fecal steroid, sitosterol, ergosterol, rapeseed sterol, soybean sterol, tomatidine, ursolic acid, alpha-tocopherol, and combinations thereof; and (c) a polymer-conjugated lipid.

7. The composition of claim 6, wherein the neutral lipid is DSPC, the steroid is cholesterol, and the polymer-conjugated lipid is a pegylated lipid.

8. The composition of claim 7, wherein the pegylated lipid is 1,2-dimyristoyl-sn-glycerol methoxypolyethylene glycol (PEG-DMG).

9. The composition of claim 6, wherein the polymer-conjugated lipid is a pegylated lipid.

10. The composition of claim 9, wherein the pegylated lipid is 1,2-dimyristoyl-sn-glycerol methoxypolyethylene glycol (PEG-DMG).

11. The composition of claim 6, wherein the therapeutic agent is selected from the group consisting of siRNA, aiRNA, miRNA, dsRNA, shRNA, mRNA, and mixtures thereof.

12. The composition of claim 11, wherein the RNA is an mRNA.

13. The composition of claim 4, wherein the therapeutic agent is selected from the group consisting of siRNA, aiRNA, miRNA, dsRNA, shRNA, mRNA, and mixtures thereof.

14. The composition of claim 13, wherein the RNA is an mRNA.

15. A method of treating a disorder in a mammal comprising administering to the mammal the composition of claim 6.

16. A method of treating a disorder in a mammal comprising administering to the mammal the composition of claim 4.

17. The method of claim 16, wherein the mammal is a human.

18. The compound of claim 1 selected from the group consisting of:

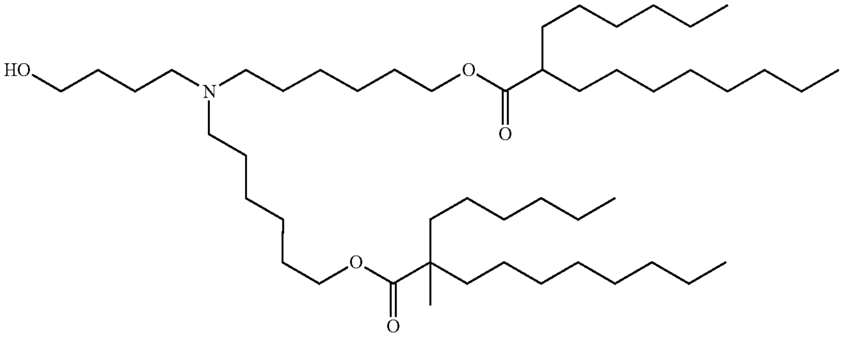

,

-continued
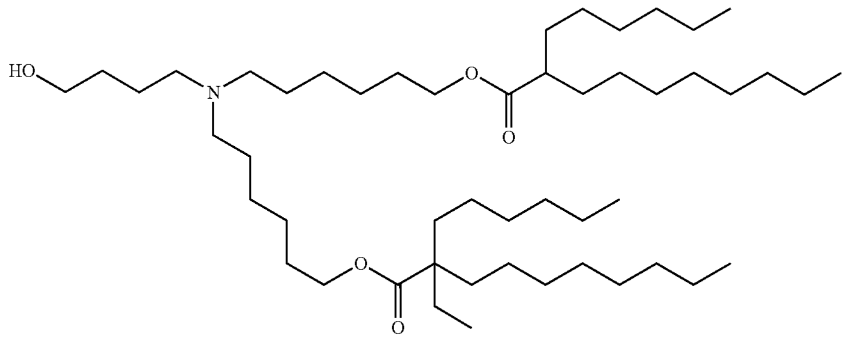
,
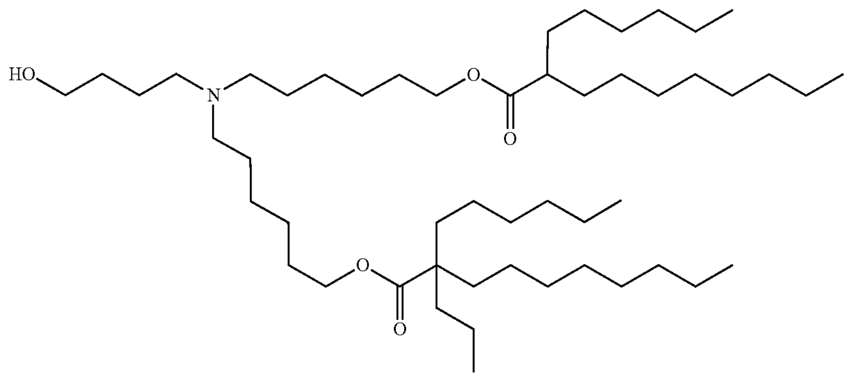
,
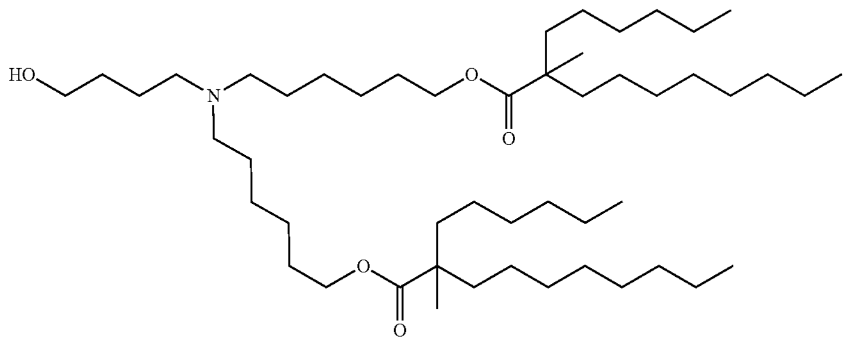
,
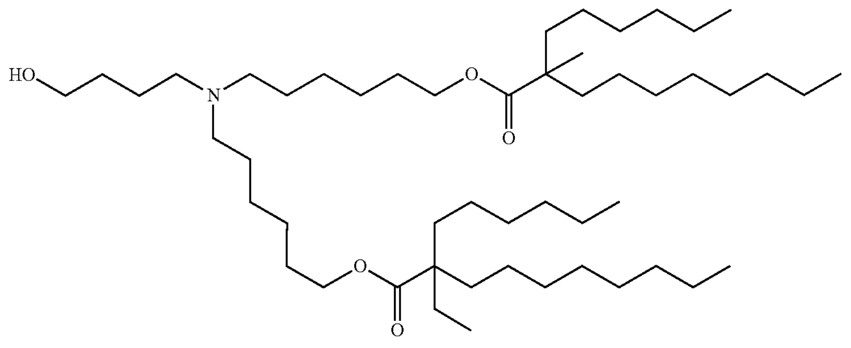
,

-continued
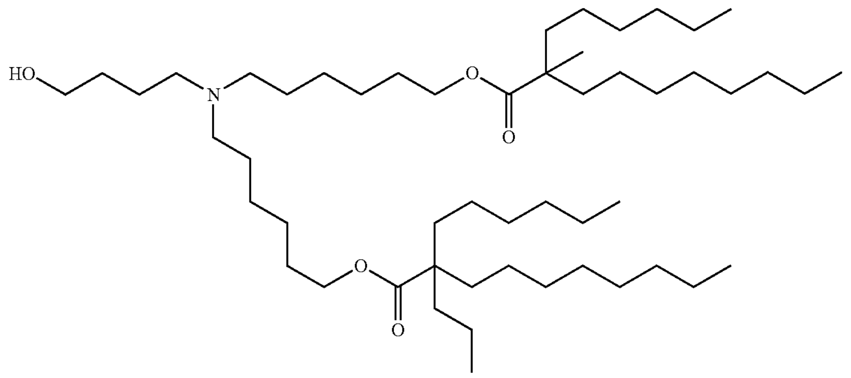
,
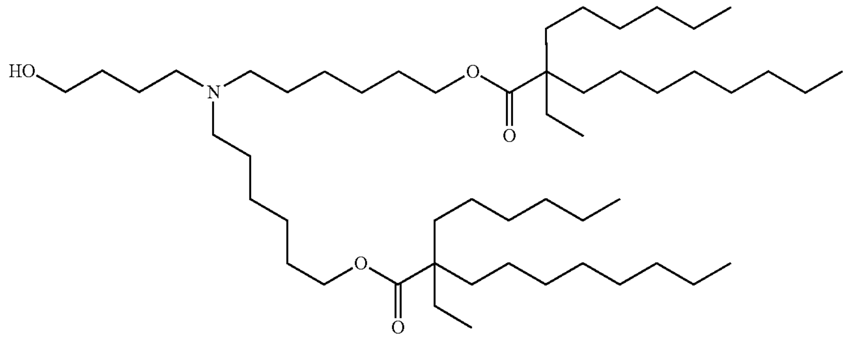
,
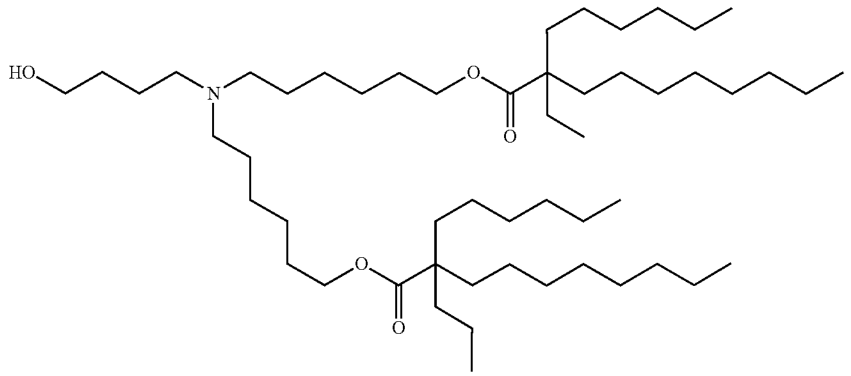
, and
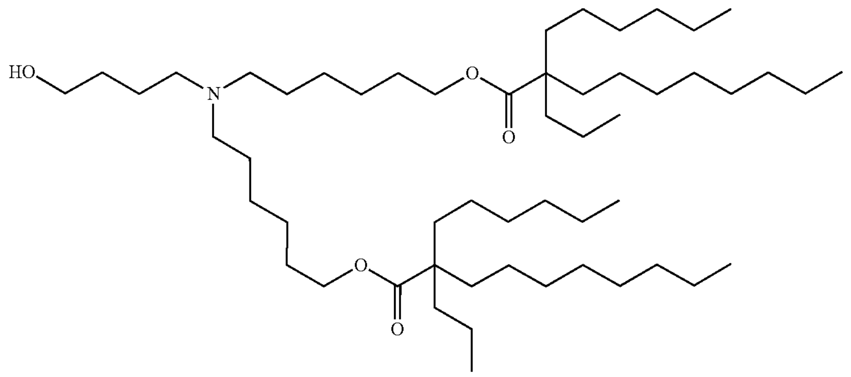
.

19. The composition of claim 6 in the form of a lipid nanoparticle.

* * * * *